United States Patent [19]
Ewing

[11] Patent Number: 5,765,564
[45] Date of Patent: Jun. 16, 1998

[54] MEDICAL LIMB SUPPORT ASSEMBLY

[76] Inventor: Brad H. Ewing, P.O. Box 87850, San Diego, Calif. 92138-7850

[21] Appl. No.: 863,288

[22] Filed: May 27, 1997

[51] Int. Cl.$^6$ ................................................. A61G 15/00
[52] U.S. Cl. ................. 128/845; 128/882; 128/DIG. 20; 602/13; 5/648
[58] Field of Search ................................ 128/845, 846, 128/877, 878, 879, DIG. 20, 882; 602/13; 5/648-651

[56] References Cited

U.S. PATENT DOCUMENTS

| | | | |
|---|---|---|---|
| 1,980,486 | 11/1934 | King | 128/882 |
| 4,090,268 | 5/1978 | Turner | 5/648 |
| 5,113,875 | 5/1992 | Bennett | 5/648 |
| 5,603,336 | 2/1997 | Shepich | 128/882 |

*Primary Examiner*—Michael A. Brown
*Attorney, Agent, or Firm*—John R. Duncan; Frank D. Gilliam

[57] ABSTRACT

A limb support assembly for typical use in supporting the legs of a person to keep the heels of a person suffering from a decubitus condition or burned areas on a limb above and out of contact with a bed. The assembly basically includes an inflatable tubular bladder, a soft absorbent sock over the bladder, attachment devices such as cords attached to the bladder ends and attachable to a bed frame, and a pump for varying bladder inflation pressure. The assembly is placed on a bed or other support at a suitable location for elevating a limb. The attachment is then installed by fastening the cords to the bed frame or other fixed part of the support. A board may be secured to the bladder assembly to further restrict movement of the assembly on the bed or other support surface.

11 Claims, 1 Drawing Sheet

MEDICAL LIMB SUPPORT ASSEMBLY

FIELD OF THE INVENTION

This invention relates to apparatus for supporting limbs, such as legs, of a human being during medical treatment for decubitus conditions and the like.

BACKGROUND OF THE INVENTION

Patients who are bedridden often develop bedsores or ulcers on their heels. These conditions are difficult to treat, particularly where the patient is in poor overall condition. Rubbing of the heels against sheets is both painful and worsens the condition of the ulcers. Similarly, burns on a limb may make raising the limb necessary to prevent a burned area from contacting the bedding. Raising the legs or an arm above the general torso level is often necessary or desirable in the treatment of other medical conditions, such as sprains or broken bones or circulatory conditions to improve the comfort of the patient.

Raising the limb with a sling fastened to an overhead cable is usually overly restrictive. The patient will be prevented from rolling to the side or otherwise adjusting his or her position. Lying on the back in one position for long periods is very uncomfortable and can lead to bed sores on the back of the heels.

A number of different devices have been developed to lift a limb above a bed surface. Simple pillows placed under the arm or leg are often used for short time elevation. However, where the elevation should continue for an extended period, pillows are not fully effective, since they can be easily moved out of position, allowing the ulcerated heel or other injured area to contact the bed. The degree of elevation will not be constant due to packing and compression and the pillow may slip down under the area of the limb intended to be elevated and out of contact with any surface, defeating the purpose of the pillow.

Barrett, in U.S. Pat. No. 5,085,214 describes an inflatable cushion that is wrapped around an extremity, such as around the calf to elevate a foot. While effective in lifting the limb, the wrap must be fairly tight to stay in place and will tend to prevent air from reaching the wrapped area. This is seriously disadvantageous to the patient, particularly one with ulcerated heels since it will exacerbate skin problems in the wrapped area. Further, someone will need to unwrap the cushion whenever the patient gets out of bed and rewrap it when upon return.

An appliance for spacing the legs is described by Shiflett in U.S. Pat. No. 5,418,991. Cushions are arranged in an "X" like cross section with the patient's limb between to arms of the "XI" and strapped to the limb. When the person is lying on his or her back, the appliance must be strapped below the leg and when the person desires to lie on his or her side, the appliance must be removed and refitted on the lower side of the upper leg to space the legs apart. This is cumbersome for a person needing only uniform leg elevation, since it will require frequent readjustment.

An abduction pillow for orthopedic support is detailed by Toth in U.S. Pat. No. 5,476,105. This is a large device having two side heel supports and a high central support for one leg when the patient desires to lie at least partially on his or her side. Supporting the heels is contraindicated when the patient has a heel ulceration problem. The intent of this device is to immobilize the patient's legs, opposite to the usual need for permitting reasonable leg movement while avoiding contact of ulcerated or burned areas of a limb with any surface.

An inflatable mattress having plural transverse cells that are independently inflatable is described by Viard in U.S. Pat. No. 5,560,374. This device is intended to uniformly support the entire body in a very straight orientation. All areas are in contact with the mattress and no area is elevated out of contact.

Thus, there is a continuing need for improved variable thickness and hardness supports for raising a limb to keep a selected areas, such as an ulcerated heel, a burned area, etc., out of contact with a mattress or other surface while permitting the person to arise and move about without hindrance and permitting the person to move from back to side without hindrance while preserving the limb elevation.

SUMMARY OF THE INVENTION

The above-noted problems, and others, are overcome in accordance with this invention by a support device for elevating a portion of the human body which basically comprises an inflatable tubular bladder, a soft, absorbent sock over the bladder, attachment means connected to end fittings on the bladder for attaching the support device to a bed or the like and means for inflating and deflating the bladder.

The bladder typically includes a cylindrical central portion and domed ends, although any other suitable cross section such as elliptical or rounded with one flat side, etc., may be used if desired. Eyes or other attachment means are provided on the ends of the bladder for connection to a cord or other means for attachment to a bed, chair, etc.

The sock is preferably made from a thick, absorbent material such as terry cloth, a fur-like material, a foam material (preferably with a cloth surface layer) or other physically similar materials. The sock may have any suitable thickness. Preferably, the sock will have a unique color and/or pattern so that it can be easily recognized when laundered with other things. Preferably, drawstrings or the like are provided at the ends of the sock to tighten down over the ends and maintain the sock in position over the bladder surface.

Any suitable arrangement may be used for attaching the support device to a bed or other structure. In a preferred embodiment, cords or straps are secured to the bladder end fittings and tied or otherwise fastened to an appropriate part of the structure, such as the frame of a bed, the frame of the leg support on a recliner chair, etc. The cord may be simply tied to the frame or any suitable clamp or clip, such as a conventional cam lock, may be used to secure the cord.

While in many cases the bladder in the sock can simply rest on the bed (under or over sheets or bed linen) and have the ends secured to the bed or other support. In one preferred embodiment, a board slightly longer and wider than the bladder can be placed under the bladder and the end fastening means may fasten to the board or pass through central holes in the board to further hold the bladder in place and prevent the bladder from rolling out of position. The board may also have edge notches arranged to permit the securing cord to be wrapped around and fastened to the board for ease of transporting the assembly of bladder and board.

While any suitable means may be provided for inflating, Ad deflating or varying the inflation of the bladder, for most convenience, a conventional Shrader valve is provided at at least one end of the bladder and a conventional hand pump and needle, of the sort used with bicycle tires, sports balls and the like, is used to vary bladder inflation. In order to retain the inflation needle with the assembly, preferably the needle is threaded onto a short valve extension fitting with the other end of the fitting threaded to be threadable onto a pump. The needle and valve extension fitting are secured in a conventional strap of the sort used to hold Jacobs chuck keys for hand-held power drills. The needle holding strap is fastened to a bladder end fitting. Other valves, such as a push-pull valve or twist valves as used with air mattresses may be used.

If desired, a heating pad, an ice bag, a chemical cold pack, a vibrating panel or other treating device may be placed over the bladder and under the sock to provide beneficial treatment to the portion of the limb positioned on the bladder. The treating device may be held in place by straps around the bladder, hook and loop material of the sort available under the Velcro® trademark, etc.

It is, therefore, an object of this invention to provide a convenient and effective support assembly for supporting limbs above a surface, such as a bed, to prevent contact between the surface and an ulcerated, burned, etc. area of the limb. Another object is to provide a limb support assembly in which the height of the support and the area in contact with the limb may be easily varied. A further object is to provide a limb support assembly that can be easily installed and uninstalled on a bed or other support surface. Still another object is to provide a board for attachment to the bladder to further limit movement of the assembly relative to the desired position. Yet a further object is to provide a limb support assembly that does not restrict a user's ability to turn to the side even during sleep while maintaining his or her feet in the elevated position. An additional object is to provide a limb support assembly that permits a user to get up from a bed, chair or other support structure without restriction. Another object is to provide a limb support assembly that will not crush down as would a pillow.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
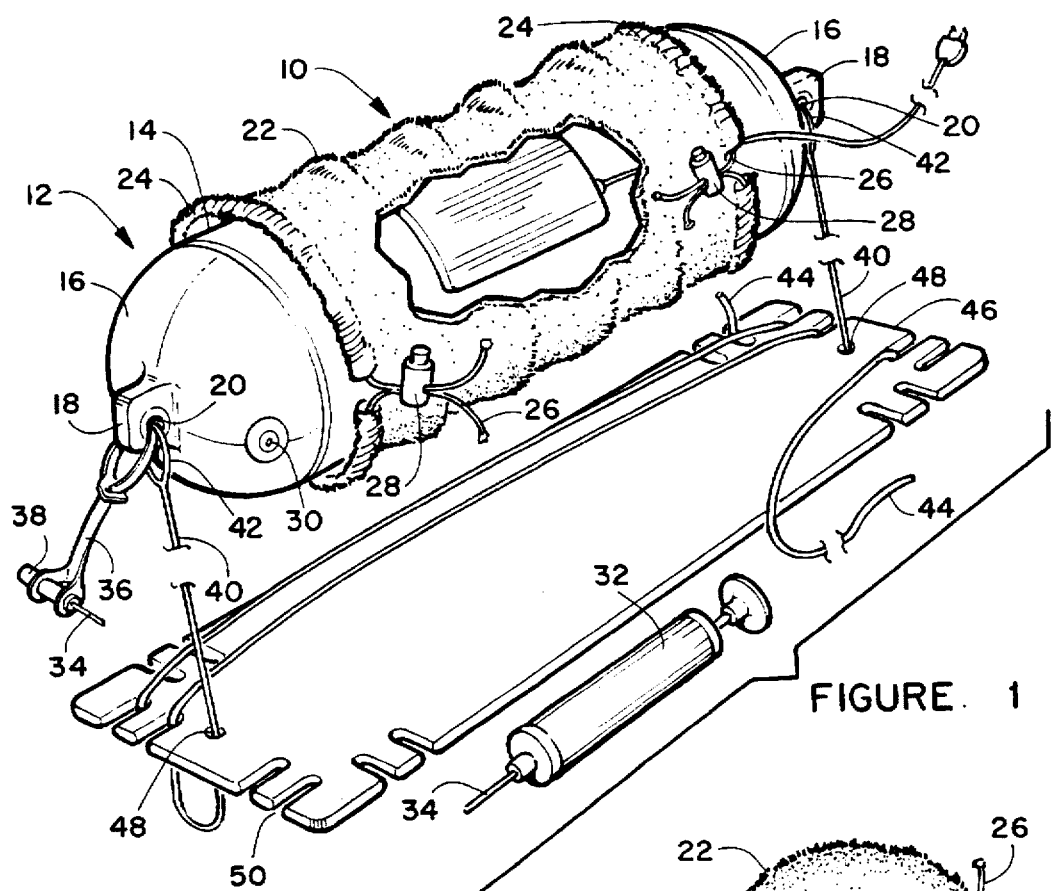
FIG. 1 is an exploded perspective view of the limb support assembly.
Figure 2:
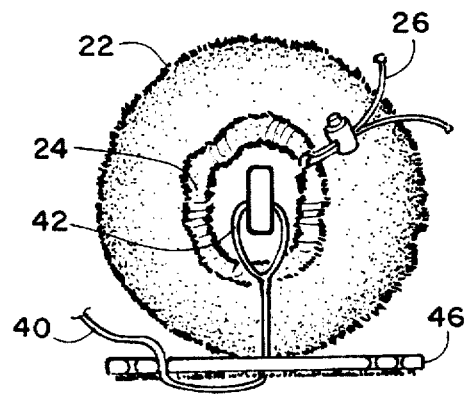
FIG. 2 is an end elevation view of the assembly.

As seen in FIG. 1, the basic limb support assembly 10 includes a tubular bladder 12 having a center section 14 and curved end sections 16. While generally a cylindrical center section 14 is preferred, any other suitable shape may be used. For example, the center section could be elliptical or could have a flat area on the side that will rest on the bed or other surface. Or, the diameter of center section 14 could vary, with two spaced narrow regions to help keep the legs in position on the device.

Bladder 12 may be formed from any suitable material, such as a vinyl, polyvinyl chloride, polyethylene or polypropylene resin. Bladders of the sort used as boating fenders with small boats are often suitable An end fitting 18, having an eye 20 is provided at each end of bladder 12. Preferably, end fittings 18 are unitary with bladder ends 16. Any other suitable end fitting 18 may be used and secured to bladder 12 in any suitable manner, such as comolding, adhesive bonding, rivets, etc.

A sock 22 of soft, absorbent material is provided in a slip fit over bladder 12. Each end of sock 22 is provided with means for tightening down over bladder ends 16 to prevent the entire sock from sliding to one end or the other. For best results, a hem 24 is formed at each end of sock 22 through which a drawstring 26 extends and which can be pulled outwardly to tighten hem 24 around end fitting 18. A suitable lock or clamp 28, such as a conventional push button clamp, is preferably used to releasably hold drawstring 26 in the tightened position. If desired, of course, the drawstring could be simply tied in the tightened position.

An inflation valve 30, such as a conventional Shrader, push-pull or twist valve is provide in at least one end 16 of bladder 12. Of these, optimum results are obtained with the Shrader type valve. A bicycle tire type or other hand pump 32 is preferably included with the assembly to change the degree of inflation of bladder 12. A conventional inflation needle 34 is shown on pump 32. A spare needle 34 may be secured to end fitting 18. A strap 36 of the sort used to mount a Jacobs chuck key on the cord of an electric drill will hold a needle 34. Typically, a needle 34 is threaded onto a short tubular adapter 38 which is internally threaded at the other end to thread onto pump 32. The adapter may not be needed, but assures that the needle will remain on strap 36.

Elongated cords 40 are attached through eyes 20 of end fittings 18 for attachment to a bed, chair or other support surface for the person using the assembly. Cords may be round, typically wrapped or knit cords or narrow flat straps, formed from any suitable material such as cotton, nylon, polypropylene or a combination thereof. While cords 40 can be attached in any suitable manner, such as simply tieing an end through eye 20, for maximum security it is preferred that an eye 42 be formed in the end of cord 40 and bonded, interwoven or have a standard eye sleeve clamp pressed over the cord and end to form a fixed eye.

Figure 3:
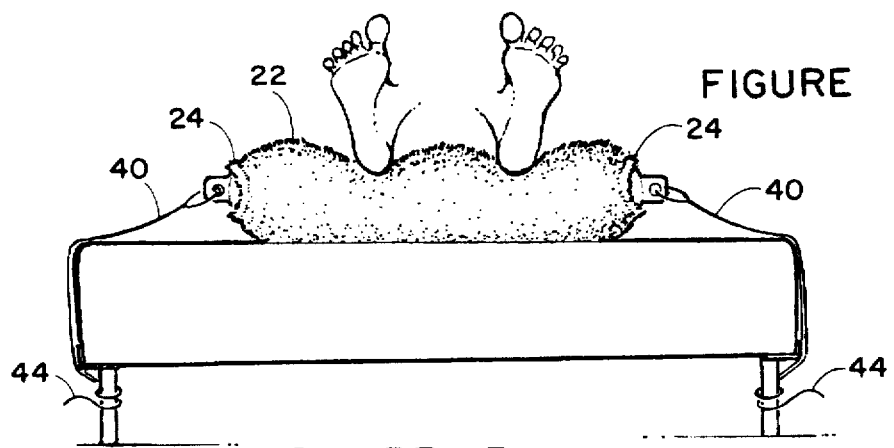
FIG. 3 is a side elevation view of the assembly in use on a bed.

The distal end 44 of cord 40 can be tied to any suitable part of the bed or other support surface, as shown in FIG. 3. Any suitable fastening means (not seen) can be used at the distal cord end as desired, such as a conventional cam clamp or other clamping or latching means.

While the assembly of, basically, bladder 12, sock 22 and cord 40 as described above can be used as shown in many cases, in some cases it is desirable to have means for further restricting movement of the assembly along a bed or other support surface.

A board 46, preferably having a configuration corresponding to that of bladder 12 but somewhat longer and wider, has holes 48 located approximately adjacent to end fittings 18 on the bladder. Cords 40 can then pass through holes 48, then to the bed frame or other structure to which the assembly is to be secured. Board 46 thus will be held tightly against the sock 22 and the assembly will be held tightly against the bed or other surface.

Board 46 can also be conveniently used to store cords 40 during transport of assembly 10. Cords 46 are passed through holes 48, then back and forth around narrow notches 50 in board 46. Notches 50 are sized to removably wedge cords 46 therein. A number of notches 50 may be provided at different locations to hold cords 40 of different lengths.

As seen in the cut away area of FIG. 1, if desired a treating pad like device 50, such as a heating pad, ice bag, vibrating pad can be placed over the surface of bladder 12 or over sock 22. For maximum comfort, the pad device 50 should be placed under sock 22. If desired, pad device 50 may be held in place by straps, hook-and-loop material or other means.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A limb support assembly, which comprises:

an inflatable, generally tubular bladder;

a soft, absorbent sock over said tubular bladder;

said sock having open ends adjacent to each end of said tubular bladder;

tightening means at each end of said sock for securing said sock over each bladder end;

a connection fitting at each end of said bladder;

fastening means connected to each said connection fitting; and means for varying the inflation of said tubular bladder.

2. The limb support assembly according to claim 1 wherein said tightening means comprises a hem around each open end of said sock, a drawstring in each hem and fastening means to secure said drawstring at a predetermined length.

3. The limb support assembly according to claim 1 wherein said connection fitting comprises a body secured to each end of said bladder and having an eye therethrough.

4. The limb support assembly according to claim 3 wherein said fastening means comprises an elongated cord secured to each of said eyes at a proximal end and having means for securing to a support means upon which said limb support assembly is placed.

5. The limb support assembly according to claim 4 wherein said support means is a bed and said distal ends are secured to a frame for said bed.

6. The limb support assembly according to claim 1 wherein said bladder is formed from a material selected from the group consisting of vinyl, polyvinyl chloride, polyethylene and polypropylene resins and combinations thereof.

7. The limb support assembly according to claim 1 wherein said sock is formed from a material selected from the group consisting of terry cloth, plastic foam, synthetic fur and combinations thereof.

8. The limb support assembly according to claim 1 wherein said inflation means comprises a Shrader valve in said bladder, a manual air pump and a needle for mounting on said pump and insertion into said Shrader valve.

9. The limb support assembly according to claim 8 further including strap means for securing a said needle to said bladder.

10. The limb support assembly according to claim 1 wherein said bladder has a cross section selected from cylinder and a cylinder having one flat side parallel to said cylinder.

11. A limb support assembly, which comprises:

an inflatable, generally tubular bladder having a cylindrical cross section and domed ends;

a soft, absorbent sock over said tubular bladder;

said sock having open ends adjacent to each end of said tubular bladder;

tightening means at each end of said sock for securing said sock over each bladder end;

an eyed connection fitting at each end of said bladder;

elongated cords connected to each said eyed connection fitting; and pump means for varying the inflation of said tubular bladder.

* * * * *